United States Patent [19]

Chou

[11] Patent Number: 5,171,883

[45] Date of Patent: Dec. 15, 1992

[54] PROCESS FOR PREPARING SULFONYL ACIDS

[75] Inventor: Yueting Chou, Chesterfield, Mo.

[73] Assignee: Monsanto Company, St. Louis, Mo.

[21] Appl. No.: 596,651

[22] Filed: Oct. 10, 1990

[51] Int. Cl.$^5$ .......................... C11D 3/39; C11D 7/38
[52] U.S. Cl. .................................................. 562/512
[58] Field of Search .......................................... 562/512

[56] References Cited

U.S. PATENT DOCUMENTS 4,758,369 7/1988 Dyroff et al. .......................... 252/94
4,824,591 4/1989 Dyroff et al. .......................... 252/94

OTHER PUBLICATIONS

J.A.C.S., 69,238-2335 Reaction of Mercaptans with Acrylic and Methacrylic Derivatives—Hurd, C. D. and Gershbein, L. L. 1947.

J.O.C. 25,1747-1752 S-Alkylmercaptosuccinic Acids—Hendrickson, J. G. and Hatch, L. F. 1960.

J.O.C. 29 (7), 1910-1915—Thiolesters—Schleppnik, A. A. and Zienty, F. B. 1963.

Primary Examiner—Arthur C. Prescott
Attorney, Agent, or Firm—R. H. Shear; R. C. Loyer; J. C. Bolding

[57] ABSTRACT

There is disclosed a process for preparing sulfonyl acids from mercaptans in a single reactor. The mercaptan is converted to a mercaptide and reacted with an acrylic acid or salt thereof in a basic reaction medium. After formation of the thioether, the reaction medium is treated with chlorine gas to oxidize the thioether to the sulfone. Mild conditions and readily available starting materials render the method capable of preparing such acids efficiently in large scale amounts.

8 Claims, No Drawings

PROCESS FOR PREPARING SULFONYL ACIDS

This invention relates to a process for preparing organic acids containing a sulfonyl group and more particularly to a process for preparing alkyl sulfonylpropionic acids.

BACKGROUND OF THE INVENTION

Derivatives of propionic acid have been employed in reactions with mercaptans to provide alkyl or aryl mercaptopropionic acids. Usually the acrylic ester or nitrile is employed in a reaction with the mercaptan to provide a thioether. In a few experiments the thioether has been oxidized to the sulfonyl derivative. A publication by C. D. Hurd and L. L. Gershbein in J.A.C.S. 69, 2328-2335 (1947) provides a typical example of such reactions.

Polycarboxylates have been employed in the salt form with a mercaptan to provide an alkyl thioether substituted polycarboxylate. The reaction is reported to provide solid derivatives which are acids and can be titrated to confirm their identity. For example, appropriate mercaptans are reacted with disodium maleate which provide solid derivatives of alkyl mercaptans. Various S-alkylmercaptosuccinic acids are reportedly prepared by J. G. Hendrickson and L. F. Hatch in J.O.C. 25, 1747-1752 (1960). Very low yields of the substituted polycarboxylate are reported.

Also, mercaptans or thiols have been reacted with acrylyl chloride to provide compounds such as 3-ethylthiopropionyl chloride. The acids are also reported to be prepared and 3-t-octylthiopropionic acid has been prepared by the reaction of t-octanethiol with acrylic acid in a basic reaction medium containing triethylamine. A relatively good yield of high purity acid was obtained. This is reported in J. Org. chem. 29 (7), 1910-1915 (1964) by A. A. Schleppnik and F. B. Zienty.

Thioethers have been known to be oxidized to the sulfone with an oxidizing agent. For large scale production it was suggested that chlorination in aqueous solution be employed to convert thioether to the sulfone. Oxidation of the crude thioether reaction product dissolved in water by means of chlorine oxidation has also been disclosed. One such example is found in *Acetylene and Carbonmonoxide Chemistry*, pp. 156 and 157.

There has recently been discovered novel sulfone mono-peroxy and diperoxy acids exhibiting extra ordinary stability and attractive properties for use as bleach for laundry detergent use. Examples of such sulfone peroxy acids are found in U.S. Pat. No. 4,758,369 and U.S. Pat. No. 4,824,591. The sulfone peroxy acids have exhibited unusually favorable properties as bleaches for detergent use in home laundry detergents. Production in large volume to supply such need has not been heretofore available. There is thus needed a convenient, efficient and safe process for preparing sulfonyl acids, the precursors for sulfone peroxy acids.

BRIEF DESCRIPTION OF THE INVENTION

In accordance with this invention there is provided a process for the preparation of sulfone acids in situ by chlorine oxidation of a thioether intermediate which was prepared from a mercaptan, sodium hydroxide and acrylic acid in a basic reaction medium.

In accordance with this invention there is provided a process for the preparation of sulfonyl acids which are, because of the purity, and ease of preparation, readily oxidized to the peracid state for use in laundry bleach compositions. In the first step a sodium mercaptide is formed by the reaction of a mercaptan and sodium hydroxide in aqueous solution. In a separate vessel sodium acrylate is prepared by addition of acrylic acid to a basic solution such as an aqueous solution of sodium carbonate. In the third step the sodium acrylate is added to the mercaptide solution with additional water if required. Sufficient energy is added to cause a reaction producing a thioether. After formation of the thioether it is conveniently oxidized by chlorine gas to provide a sulfonyl acid, which precipitates from the aqueous media.

The sulfonyl acid is conveniently recovered by filtration.

The process may be briefly described by the following reactions

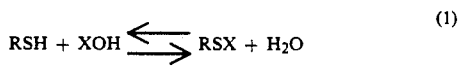

(1)

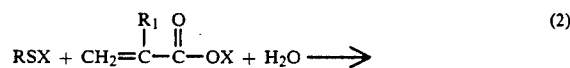

(2)

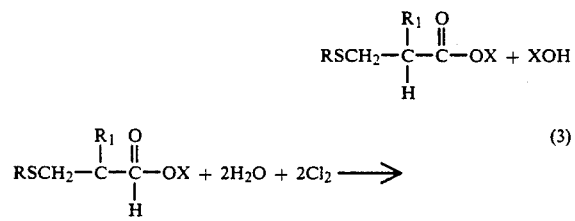

(3)

$$R-\underset{\underset{O}{\|}}{\overset{\overset{O}{\|}}{S}}-CH_2-\underset{\underset{H}{|}}{\overset{\overset{R_1}{|}}{C}}H-\overset{\overset{O}{\|}}{C}-OH + XCl + 3HCl$$

wherein R is selected from the group consisting of alkyl radicals having from 1 to 20 carbon atoms, aryl, alkyaryl, aralkyl, and cycloalkyl radicals having from 4 to 9 carbon atoms, $R_1$ is selected from the group consisting of hydrogen and alkyl radicals having from 1 to 4 carbon atoms and X is an alkali metal cation.

DETAILED DESCRIPTION OF THE INVENTION

In accordance with this invention, there is provided a process wherein mild conditions are employed and a single reactor for all steps is provided. Because of this simplification, sulfonyl acids are provided economically and in such high yield that large scale production is possible.

In the first step, a mercaptide is formed by the reaction of a mercaptan with an appropriate alkali metal, such as sodium or potassium. The alkali metal employed may be in the solid form, although highly concentrated solutions, such as the hydroxide, may be employed. However, the introduction of aqueous solutions of the alkali metal hydroxide is generally the most convenient.

In the preferred mode the mercaptide is formed by adding the alkyl mercaptan to an aqueous caustic solution at a concentration of about 10% at relatively low temperatures such as in the range of from 5° C. to about 15° C. The reaction is carried out at ambient temperature forming a relatively thick slurry. It is noted that agitation of the reaction mixture such as by stirring at high speeds tends to produce an undesirably thick slurry whereas agitation at slower speeds maintains the slurry at a manageable viscosity. Further, temperature does not appear to affect the viscosity of the mercaptan/mercaptide mixture in the range of from about 10° C. to about 60° C. The addition of a small amount of water reduces the viscosity of the slurry. However, the addition of water will result in the formation of two layers at higher temperatures such as in the range of from about 25° C. to about 30° C. The upper layer containing only the alkyl mercaptan.

In a separate vessel the alkali metal salt of acrylic acid is prepared by adding acrylic acid to one equivalent of a basic salt or base. Preferably sodium carbonate is employed but other alkali metal bases such as sodium or potassium hydroxide may be employed. This reaction is conducted at room temperature with stirring continuing for a brief period after the completion of the addition of the acrylic acid.

The alkyl thiopropionate is prepared easily even when the acrylic acid salt is prepared separately and is introduced into the aqueous solution of mercaptide with additional water. It has been found that because of the high electrophilicity of sodium acrylate toward mercaptide the reaction proceeds toward the formation of the thioether. However, in the reaction of the mercaptide with substituted acrylic acid such as methacrylic acid, crotonic acid or itaconic acid, it has been found water concentration is critical. In the case of methacrylic acid the water concentration should be controlled so as not to exceed about 50% of the reaction medium to obtain a reasonable yield.

The reaction of the acrylate with mercaptide takes place at a temperature in the range of from about 10° C. to about 20° C. but to assure complete reaction, it is usual to heat the reaction mixture to assure complete reaction. Heating to temperatures in the range of from about 50° C. to about 80° C., preferably about 75° C. with vigorous stirring reduces side reactions and resulting impurities. Foaming of the reaction mixture is controlled by intermittent interruption of the agitation to allow the reaction mixture to settle.

Without isolating the thioether from the reaction medium in which it is formed, the sulfonyl compound is easily prepared by oxidation with chlorine gas. Chlorine gas is passed through the aqueous medium at a temperature in the range of from about 45° C. to about 60° C. and preferably in the range of from about 50° C. to about 55° C. The reaction takes place in basic aqueous medium at a pH in the range of from about 10 to about 13. Since the reaction is exothermic external cooling is applied to control the reaction temperature. It has also been found that vigorous agitation is required to provide complete reaction of the thioether. The reaction usually takes place quickly and is completed within less than 30 minutes. Typically the reaction can be completed, with efficient cooling and agitation in a period of from about 10 to about 15 minutes.

Because the final sulfone product is a solid and precipitates from solution as it is formed, water is added to the reactor during chlorine oxidation. Addition of water controls the viscosity of the reaction mixture and aids in the efficient agitation and resultant completeness of reaction of the thioether intermediate. Because the reaction is efficient, oxidation is completed when the chlorine scrubber indicate the presence of chlorine gas in the reactor's upper space. At the completion of the reaction the temperature of the reaction mixture will decline gradually because it is desirable to employ an efficient cooling system for the exothermic reaction. To assure complete oxidation, it is preferred to employ an excess of chlorine gas.

The sulfone product can be isolated easily due to its low solubility in water. Separation by conventional means such as filtration or centrifugation provides an efficient means to obtain the product. Drying of the filter cake should be carried out at relatively lower temperatures to prevent a color change of the product. It has been determined that a slight brown color can occur at temperatures in excess of about 40° C. In most detergent applications, coloration of the product is undesirable. Therefore, slower drying at relatively lower temperatures is preferred.

In accordance with the above described procedure, highly pure (97%) sulfone propionic acids can be prepared in high yields (95-96%).

The invention will be best understood by the following examples which illustrate, but which do not limit the practice and effectiveness of the process of this invention.

EXAMPLE 1

Sodium acrylate is prepared by charging 27.67 grams of sodium carbonate and 200 ml. of water to a 500 ml. round bottomed flask. At room temperature there was added dropwise 36 g. of acrylic acid. The mixture was then transferred to a 500 ml. addition funnel. Sodium octylmercaptide was formed by adding 45.86 g. of 50% sodium hydroxide solution and 190 ml. of water to a 2 l., 4-neck round bottomed flask equipped with a condenser, overhead stirrer, thermometer and an addition funnel. After cooling the caustic solution to about 18° C., 73 g. of octylmercaptan was added slowly with moderate agitation. After formation of the mercaptide, the sodium acrylate solution was added to the thick, white mercaptide slurry which was held at a temperature of about 10° C. The mixture was stirred vigorous for about 30 minutes after which the system was heated to about 72° C. for an additional 30 minutes. When the reaction was determined to be complete, about 200 ml. of water were added to the reactor and the system cooled to about 50° C. With cooling by an ice bath, chlorine gas was bubbled through the vigorous agitated solution while the temperature was maintained at about 50° C. Chlorine oxidation was completed in about 10 minutes and the solution became a white slurry. The reaction medium was cooled to about 10° C. and filtered. The filter wet cake was reslurried with cold water twice and filtered. The wet cake was then dried at room temperature yielding 120.7 g. of dry product indicating a yield of about 96.6%. Product purity was indicated by HPLC analysis as 97% pure octylsulfonylpropionic acid demonstrating a melting point of 120° C. Analysis of the product in weight percent found C:52.2 H:8.86, and S:12.54 as compared to theory of C:52.8, H:8.8, and S:12.8.

EXAMPLE 2

(Prior Art)

This example demonstrates the criticality of the addition of sufficient base to the reaction mixture containing the mercaptide and acrylic acid.

To a 100 cc round bottomed flask was charged 5.36 g Na2CO3 and 40 cc water. To the solution at room temperature was added dropwise 7.2 g of acrylic acid. Then the mixture was transferred to an addition funnel.

To a 500 cc 4-neck flask which was equipped with condenser, overhead stirrer, thermometer and an addition funnel was charged 42.4 g water. At 18° C. 14.6 g octyl mercaptan was added with fast agitation. Then sodium acrylate solution was added to the system at 10° C. Addition took about 30 minutes. The mixture was heated to 75° C. and was held there for 2 hours. It appeared as two layers and the top layer was octylmercaptan. 200 cc of water was added to the reactor. At 48° C., chlorine gas was bubbled through the vigorously agitated mixture. The off gas was scrubbed with NaOH solution. Chlorine oxidation was completed in about ten minutes at 50°-60° C. The mixture was cooled to 20° C. and filtered and dried in the filter under vacuum suction. Only 1.2 g of dry product was obtained (5% yield). The major side product was octyl sulfonylchloride which as the result from the chlorination on the unreacted octyl mercaptan.

EXAMPLE 3

In equipment as described in Example 1, there were charged 16.17 g of 50% sodium hydroxide and 20 ml of water. After cooling to 10° C., 14.6 g of octyl mercaptan were added dropwise. To the white slurry were added 8.6 g of methacrylic acid over a period of about 10 minutes. Upon completion of the addition, the reactor was heated to about 75° C. whereupon the slurry became a cloudy solution. After holding the solution at 75 for 2 hours it was diluted with 100 ml of water and cooled to about 45° C. After fitting the flask with an ice bath for efficient cooling, chlorine gas was bubbled through the agitated solution. Chlorine oxidation was completed in about 20 minutes and the slurry was cooled to 10° C. then filtered. The filter wet cake was reslurried with cold water and again filtered. The wet cake from the second filtration was air dried at room temperature to provide 21.87 g of product (82.5% yield). The dried product was recrystallized from toluene and exhibited a melting point of 91-93 C. HPLC analysis indicated the purity to be about 81%.

Although the invention has been described with respect to specific examples of reagents, conditions and equipment, other equivalent compositions and conditions can be utilized without departing from the scope of this invention.

I claim:

1. A process for the production of alkyl sulfonyl propionic acid in one reactor which comprises reacting an alkyl mercaptide represented by the formula

RSX wherein R is an alkyl radical having from 1 to 20 carbon atoms and X is an alkali metal, with acrylic acid represented by the formula

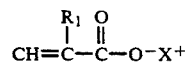

wherein $R_1$ is selected from the group consisting of hydrogen and an alkyl radical having from 1 to 4 carbon atoms and X is an alkali metal, in a basic aqueous reaction medium containing greater than an equimolar amount of base with respect to said acid and at a temperature in the range of from about 10° C. to about 20° C. and then oxidizing the resulting thioether with chlorine gas in said aqueous medium initially at a pH in the range of from about 10 to about 13 whereby an alkyl sulfonylpropionic acid is formed.

2. The process of claim 1 wherein R is an alkyl radical having from 5 to 10 carbon atoms.

3. The process of claim 2 wherein the alkyl radical is octyl.

4. The process of claim 1 wherein $R_1$ is methly.

5. The process of claim 1 wherein R hydrogen.

6. The process of claim 1 wherein R is octyl and $R_1$ is hydrogen.

7. The process of claim 1 wherein X is sodium.

8. The process of claim 1 wherein the temperature of the oxidation reaction is in the range of from about 45° C. to about 80° C.